United States Patent
West

(10) Patent No.: US 6,306,202 B1
(45) Date of Patent: Oct. 23, 2001

(54) WATER SOLUBLE FIXED COPPER-BORAX WOOD PRESERVATIVE COMPOSITION

(76) Inventor: Michael Howard West, 54 S. Crockett Rd., Senatobia, MS (US) 38668

( * ) Notice: Subject to any disclaimer, the term of this patent is extended or adjusted under 35 U.S.C. 154(b) by 0 days.

(21) Appl. No.: 09/606,441

(22) Filed: Jun. 30, 2000

(51) Int. Cl.[7] .............................. A01N 59/14; A01N 59/20
(52) U.S. Cl. .................. 106/18.3; 252/385; 424/630; 424/632; 424/633; 424/634; 424/635; 424/637; 424/657; 424/658; 424/660
(58) Field of Search ................................. 106/18.3, 18.32; 252/381, 385; 424/630, 632, 633, 634, 635, 637, 657, 658, 660

(56) References Cited

U.S. PATENT DOCUMENTS

| | | | |
|---|---|---|---|
| 4,661,157 | * | 4/1987 | Beauford et al. ................. 106/18.13 |
| 4,759,872 | * | 7/1988 | Marx et al. ............................. 24/630 |
| 5,078,912 | * | 1/1992 | Goettsche et al. ................. 252/400.1 |
| 5,342,438 | * | 8/1994 | West .................................... 106/18.3 |

* cited by examiner

*Primary Examiner*—Anthony Green

(57) ABSTRACT

A water soluble fixed copper-borax wood preservative composition which comprises a fixed copper compound chosen from the group consisting of copper oxides, copper hydroxide, basic copper carbonate, basic copper sulfate, and copper oxychloride combined in water with sodium tetraborate decahydrate wherein the fixed copper compound concentration ranges from 0.01 parts to 0.20 parts for each part of sodium tetraborate decahydrate, plus a method for preparing the composition described above which comprises milling the fixed copper compound with the sodium tetraborate decahydrate in water.

2 Claims, No Drawings

WATER SOLUBLE FIXED COPPER-BORAX WOOD PRESERVATIVE COMPOSITION

CROSS REFERENCE TO RELATED APPLICATIONS

NOT APPLICABLE

STATEMENT REGARDING FEDERALLY SPONSORED RESEARCH OR DEVELOPMENT

NOT APPLICABLE

REFERENCE TO A MICROFICHE APPENDIX

NOT APPLICABLE

BACKGROUND OF THE INVENTION

The subject matter of the claimed invention pertains to a water soluble fixed copper-borax wood preservative composition and to methods for preparing this wood preservative composition. Borax is the common name for sodium tetraborate decahydrate. Fixed copper compounds are listed in the literature as including copper oxides, copper hydroxide, basic copper carbonate, basic copper sulfate, and copper oxychloride.

As their name implies, fixed copper compounds are water insoluble. To be effective solid wood preservative, fixed copper compounds must be rendered water soluble. This is commonly accomplished by complexing the fixed copper compounds with ammonia or amines. Ammonia and amines add significantly to the health and environmental hazards posed by fixed copper wood preservatives and their elimination will be welcome in the wood preservation industry. Ammonia and amines also encourage the growth of certain wood defacing fungi. These molds require the use of mildewcides when wood is treated during hot, humid weather; and this adds to treating costs.

Borax is a readily available water soluble wood preservative, and it is found in commerce combined with fixed copper compounds which have been made water soluble by adding ammonia or amines. It has not been previously known to use fixed copper compounds combined with borax, wherein the fixed copper compound is not complexed with ammonia or amines, for wood preservation. Borax has limited solubility in water and the commercial product is slow to dissolve. It is believed the limited solubility of borax as well as the difficulty in preparing water soluble complexes of fixed copper compounds and borax has previously hidden their usefulness from those skilled in the art of wood preservation.

Wood preservatives are frequently used in conjunction with water repellents, and these wax emulsions often contain small amounts of ammonia or amines. The levels of ammonia or amines in water repellents are not sufficient to form water soluble fixed copper complexes in fixed copper treating solutions.

Wood preservatives for use in waferboard need not be completely water soluble. Fixed copper compounds used in waferboard preservation do show increased protection where at least some of the fixed copper compound is water soluble. Small amounts of water insoluble fixed copper compounds are not objectionable in solid wood preservatives so long as their particle size is small enough to penetrate the wood.

BRIEF SUMMARY OF THE INVENTION

My invention teaches a water soluble fixed copper-borax wood preservative composition which comprises a fixed copper compound chosen from the group consisting of copper oxides, copper hydroxide, basic copper carbonate, basic copper sulfate, and copper oxychloride combined in water with sodium tetraborate decahydrate wherein the fixed copper compound concentration ranges from 0.01 parts to 0.20 parts for each part of sodium tetraborate decahydrate. It also teaches a method for preparing this water soluble wood preservative which comprises milling the borax with the fixed copper compound in water.

DETAILED DESCRIPTION OF THE INVENTION

In the preferred embodiment of my invention the water soluble fixed copper-borax wood preservative composition contains about 3 parts copper hydroxide, about 43 parts borax, and about 54 parts water. For pressure treating wood this preferred composition is diluted to a 1 to 4% concentration in water. For preserving waferboard this composition is used undiluted and added to wood wafers in the mixing hopper by any convenient means. For diffusion treating of unseasoned lumber this composition is coated undiluted on the wood surface, and the treated lumber shrouded in plastic about 3 weeks for thorough penetration.

In the preferred embodiment for the preparation of the composition of my invention the fixed copper compound, the borax, and the water are blended together without concern for order of addition, and the dispersion milled together at high speed. Dispersers used in the paint industry for reducing pigment particle size are the preferred milling equipment. Milling time needed varies upon disperser blade tip speed; but should not exceed one hour. Fixed copper compound water solubility is determined by diluting the milled composition to a 4% concentration in water and examining the dilution visually for clarity. So long as copper compound particles do not settle from the dilution in one hour the composition is suitable for pressure treating and diffusion treating of solid wood. For treating waferboard up to half of the copper compound can settle in one hour.

Water repellents and fixing agents for the borax may be used with compositions of my invention when treating wood. Ammonia or amines may not be added to the compositions in quantities sufficient to form complexes with the fixed copper compounds. Other chemicals may be added to improve the water solubility of the fixed copper compounds or of the borax. Mildewcides and other compatible wood preservatives may be used with the composition of my invention in wood treating.

I claim:

1. A water soluble fixed copper-borax wood preservative composition which comprises a fixed copper compound selected from the group consisting of copper oxides, copper hydroxide, basic copper carbonate, basic copper sulfate, and copper oxychloride combined in water with sodium tetraborate decahydrate wherein the fixed copper compound concentration ranges from 0.01 parts to 0.20 parts for each part of sodium tetraborate decahydrate.

2. A method for preparing a water soluble fixed copper-borax wood preservative composition which comprises milling together in water a fixed copper compound, selected from the group consisting of copper oxides, copper hydroxide, basic copper carbonate, basic copper sulfate, and copper oxychloride, with sodium tetraborate decahydrate wherein the fixed copper compound concentration ranges from 0.01 parts to 0.20 parts for each part of sodium of sodium tetraborate decahydrate.

* * * * *